(12) United States Patent
Dahl et al.

(10) Patent No.: US 8,569,499 B2
(45) Date of Patent: Oct. 29, 2013

(54) PROCESS FOR MAKING TRANS-1-((1R,3S)-6-CHLORO-3-PHENYLINDAN-1-YL)-3,3-DIMETHYLPIPERAZINE

(75) Inventors: Allan Carsten Dahl, Nyrup (DK); Christina Wøhlk Nielsen, Copenhagen Ø (DK); Christina Suteu, Illkirch (FR); David Robin, Strasbourg (FR); Peter Brøsen, Herlev (DK)

(73) Assignee: H. Lundbeck A/S, Valby (DK)

( * ) Notice: Subject to any disclaimer, the term of this patent is extended or adjusted under 35 U.S.C. 154(b) by 908 days.

(21) Appl. No.: 11/816,383

(22) PCT Filed: Feb. 14, 2006

(86) PCT No.: PCT/DK2006/000086
§ 371 (c)(1),
(2), (4) Date: Feb. 11, 2008

(87) PCT Pub. No.: WO2006/086984
PCT Pub. Date: Aug. 24, 2006

(65) Prior Publication Data
US 2008/0153847 A1    Jun. 26, 2008

Related U.S. Application Data

(60) Provisional application No. 60/653,428, filed on Feb. 16, 2005.

(30) Foreign Application Priority Data

Feb. 16, 2005   (DK) ................................ 2005 00237

(51) Int. Cl.
*C07D 295/00* (2006.01)
(52) U.S. Cl.
USPC ......................................................... 544/403
(58) Field of Classification Search
USPC ...................................... 514/255.03; 544/403
See application file for complete search history.

(56) References Cited

U.S. PATENT DOCUMENTS

| 4,031,216 | A  | 6/1977  | Cyrus et al.     |
|-----------|----|---------|------------------|
| 4,443,448 | A  | 4/1984  | Bogeso           |
| 4,616,086 | A  | 10/1986 | Witte et al.     |
| 5,026,853 | A  | 6/1991  | Van Daele et al. |
| 5,466,806 | A  | 11/1995 | Belleau et al.   |
| 5,561,057 | A  | 10/1996 | Trani et al.     |
| 5,807,855 | A  | 9/1998  | Bogeso et al.    |
| 5,807,897 | A  | 9/1998  | Warawa et al.    |
| 6,103,719 | A  | 8/2000  | Esser et al.     |
| 6,153,611 | A  | 11/2000 | Mattson et al.   |
| 6,410,794 | B1 | 6/2002  | Zinnen et al.    |
| 6,444,854 | B1 | 9/2002  | Dapremont et al. |
| 6,455,736 | B1 | 9/2002  | Zinnen et al.    |
| 6,506,940 | B1 | 1/2003  | Jadav et al.     |
| 6,635,645 | B1 | 10/2003 | Lochead et al.   |
| 7,648,991 | B2 | 1/2010  | Bang-Andersen et al. |
| 7,767,683 | B2 | 8/2010  | Lopez De Diego et al. |
| 7,772,240 | B2 | 8/2010  | Bang-Andersen et al. |
| 2010/0105699 | A1 | 4/2010 | Bang-Andersen et al. |

FOREIGN PATENT DOCUMENTS

| EP | 0035363 |   | 9/1981 |
|----|---------|---|--------|
| EP | 0035363 | * | 5/1985 |
| EP | 0638073 | * | 4/1993 |

(Continued)

OTHER PUBLICATIONS

Gu, et al., Design, Synthesis, and Monoamine Transporter Binding Site Affinities of Methoxy Derivatives and Indatraline, J. Med. Chem. 43, 4868-4876 (2000).*

(Continued)

*Primary Examiner* — Erich A Leeser
(74) *Attorney, Agent, or Firm* — Mary Catherine Di Nunzio; Margaret M. Buck

(57) ABSTRACT

Described is a method for making the trans-1-((1R,3S)-6-chloro-3-phenylin-dan-1-yl)-3,3-dimethylpiperazine (formula I) and salts thereof and a similar method for making 4-((1R,3S)-6-chloro-3-phenylin-dan-1-yl)-1,2,2-trimethylpiperazine (formula IX) and salts thereof, which method comprises conversion of a compound of formula IVa to the compound of formula I or the compound of formula IX, respectively.

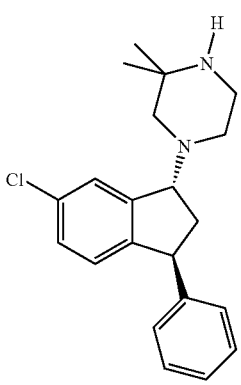

(I)

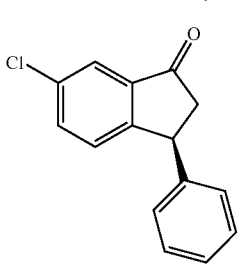

(IVa)

55 Claims, No Drawings

(56) References Cited

FOREIGN PATENT DOCUMENTS

| | | | |
|---|---|---|---|
| EP | 0638073 | B1 | 6/2000 |
| JP | 06-184132 | A | 5/1994 |
| JP | 2000/351773 | A | 12/2000 |
| WO | 93/08799 | A1 | 5/1993 |
| WO | 93/22293 | A1 | 11/1993 |
| WO | 95/15299 | A1 | 6/1995 |
| WO | 99/42107 | A1 | 8/1999 |
| WO | 99/61426 | A1 | 12/1999 |
| WO | 99/62893 | A2 | 12/1999 |
| WO | 00/12073 | A1 | 3/2000 |
| WO | 00/34284 | A1 | 6/2000 |
| WO | 00/75172 | A2 | 12/2000 |
| WO | 00/76961 | A1 | 12/2000 |
| WO | 00/78708 | A1 | 12/2000 |
| WO | 2005/016900 | A1 | 2/2005 |
| WO | 2005/016901 | A1 | 2/2005 |
| WO | WO 2005/016901 | * | 2/2005 |
| WO | 2006/086985 | A1 | 8/2006 |
| WO | 2006/086986 | A1 | 8/2006 |

OTHER PUBLICATIONS

Bogeso, Neuroleptic Activity and Dopamine-Uptake Inhibition in 1-Piperazino-3-phenylindans, J. Med. Chem., 26, 935-947 (1983).*

Balsara, J. J, et al. Effect of Drugs Influencing Central Serotonergic Mechanisms on Haloperidol-Induced Catalepsy. Psychopharmacol. 1979. 62:67-69.

Bertz, R. J. et al. Use of in Vitro and in Vivo Data to Estimate the Likelihood of Metabolic Pharmacokinetic Interactions. Clin. Pharmacokinet. 1997. 32(3):210-258.

Bogeso, K. P. Drug Hunting: The Medicinal Chemistry of 1-Piperazino-3-Phenylindans and Related Compounds. Copenhagen, Denmark: Nørhaven. 1998. (Thesis). ISBN 87-88085-10-4.

Bogeso, K. P. et al. Enhanced D1 Affinity in a Series of Piperazine Ring Substituted 1-Piperazino-3-Arylindans with Potential Atypical Antipsychotic Activity. J. Med. Chem. 1995. 38(22):4380-4392.

Bogeso, K. P. et al. 3-Phenyl-1-indanamines. Potential Antidepressant Activity and Potent Inhibition of Dopamine, Norepinephrine, and Serotonin Uptake. J. Med. Chem. 1985. 28:1817-1828.

Bogeso, K. P. Neuroleptic Activity and Dopamine-Uptake Inhibition in 1-Piperazino-3-phenylindans. J. Med. Chem. 1983. 26(7):935-47.

Carlsson, A. Antipsychotic Drugs, Neurotransmitters, and Schizophrenia. Am. J. Psych. 1978. 135(2):164-173.

Carlsson, L. et al. QTU-Prolongation and Torsades de Pointes Induced by Putative Class III Antiarrhythmic Agents in the Rabbit Etiology and Interventions. J. Cardiovasc. Pharmacol. 1990. 16:276-285.

Chauret, N. et al. The Use of 3-[2-(N,N-Diethyl-N-Methylammonium)Ethyl]-7-Methoxy-4-Methylcoumarin (AMMC) as a Specific CYP2D6 Probe in Human Liver Microsomes. Drug Metab. Dispos. 2001. 29(9):1196-1200.

Clark, W. M. et al. A Highly Enantioselective Conjugate Reduction of 3-Arylinden-1-ones Using Bakers' Yeast for the Preparation of (S)-3-Arylindan-1-ones. Org. Lett 1999. 1(11):1839-1842.

Clark, W. M. et al. A Catalytic Enantioselective Synthesis of the Endothelin Receptor Antagonists SB-209670 and SB-217242. A Base-Catalyzed Stereospecific Formal 1,3-Hydrogen Transfer of a Chiral 3-Arylindenol. J. AM. Chem. Soc. 1998. 120:4550-4551.

Cossy, J. et al. Synthesis of Indatraline Using a Suzuki Cross-Coupling Reaction and a Chemoselective Hydrogenation: A Versatile Approach. Synlett 2003. 10:1515-1517.

Cox, G.B. (ed.) Preparative Enantioselective Chromatography. Oxford, UK: Blackwell Publishing Ltd. 2005.

Darpö, B. Spectrum of Drugs Prolonging QT Interval and the Incidence of Torsades de Pointes. Eur. Heart J. Suppl. 2001. (3 suppl. K):K70-K80.

Davies, H. M. L. et al. Asymmetric Synthesis of (+)-Indatraline Using Rhodium-Catalyzed C-H Activation. Tet. Lett. 2002. 43:4951-4953.

Eder, D. N. CEE-03-310 CeNeS Pharmaceuticals. Curr. Opin. Invest. Drugs. 2002. 3(2): 284-288.

Ereshefsky, L. et al. Serotonin Selective Reuptake Inhibitor Drug Interactions and the Cytochrome P450 System, J. Clin. Psych. 1996. 57(Suppl. 8):17-25.

Froimowits, M. et al. Slow-Onset, Long-Duration 3-(3',4'-Dichlorophenyl)-1-indanamine Monoamine Reuptake Blockers as Potential Medications to Treat Cocaine Abuse. J. Med. Chem. 2000. 43:4981-4992.

Glassman, A. H. et al. Antipsychotic Drugs: Prolonged QTc Interval, Torsade de Pointes, and Sudden Death. Am J Psychiatry. 2001. 158(11):1774-1782.

Gu, X. H. et al. Design, Synthesis, and Monoamine Transporter Binding Site Affinities of Methoxy Derivatives of Indatraline. J. Med. Chem. 2000. 43:4868-4876.

Haleblian, J. et al. Pharmaceutical Applications of Polymorphism. J. Pharmaceut. Sci. 1969. 58(8):911-929.

Hyttel, J. et al. Neurochemical Profile of Lu 19-005, a Potent Inhibitor of Uptake of Dopamine, Noradrenaline, and Serotonin. J. Neurochem. 1985. 44:1615-1622.

Lin, J. H. et al. Role of Pharmacokinetics and Metabolism in Drug Discovery and Development. Pharmacol. Rev. 1997. 49(4):403-449.

Millan, M. J. et al. S18327 (1-{2-[4-(6-Fluoro-1,2-benzisoxazol-3-yl)piperid-1-yl]ethyl}3-phenyl imidazolin-2-one), a Novel, Potential Antipsychotic Displaying Marked Antagonist Properties at α1- and α2-Adrenergic Receptors: I. Receptorial, Neurochemical, and Electrophysiological Profile. J. Pharmacol. Exp. Ther. 2000. 292(1):38-53.

Pedersen, V. et al. Drug Hunting. Ch. 25. In Interviews by D. Healy. The Psychopharmacologists II. London: Arnold. 1999. pp. 561-579.

Raehl, C. L. et al. Drug-Induced Torsade de Pointes. Clin. Pharm. 1985. 4:675-690.

Rendic, S. et al. Human Cytochrome P450 Enzymes: A Status Report Summarizing Their Reactions, Substrates, Inducers, and Inhibitors. Drug Metab. Rev. 1997. 29(1&2):413-580.

Seeman, P. Dopamine Receptors and Psychosis. Sci. Am. 1995. 2:28-37.

Shulman, R. W. et al. Psychotropoic Medications and Cytochrome P450 2D6: Pharmacokinetic Considerations in the Elderly. Can. J. Psychiatry. 1997. 42(suppl. 1):4S-9S.

Sommer, M. B. et al. Application of (2-Cyanoaryl)arylacetonitriles in Cyclization and Annulation Reactions. Preparation of 3-Arylindans, 4-Aryl-3,4-dihydronaphthatenes, 4-Arylisoquinolines, 1-Aminonaphthalenes, and Heterocyclic Analogues. J. Org. Chem. 1990. 55:4822-4827.

Willner, P. Dopamine and Depression: A Review of Recent Evidence. I. Empirical Studies. Brain Res. Rev. 1983. 6 (3):211-224.

Willner, P. Dopamine and Depression: A Review of Recent Evidence. II. Theoretical Approaches. Brain Res. Rev. 1983. 6(3):225-236.

Willner, P. Dopamine and Depression: A Review of Recent Evidence. III. The Effects of Antidepressant Treatments. Brain Res. Rev. 1983. 6(3):237-246.

Woosley, R. L. Cardiac Actions of Antihistamines. Ann. Rev. Pharmacol. Toxicol. 1996. 36:233-252.

Yap, Y. G. et al. The Current Cardiac Safety Situation With Antihistamines. Clin. Exper. Allergy. 1999. 29(suppl. 1):15-24.

Yun, J. et al. Efficient Kinetic Resolution in the Assymetric Hydrosilylation of Imines of 3-Substituted Indanones and 4-Substituted Tetralones. J. Org. Chem. 2000. 65:767-774.

International Search Report for International Application No. PCT/DK2006/000086. May 22, 2006.

Gonzalez-Gomez, J.C. et al. New Arylpiperazine Derivatives with High Affinity for alpha 1A, D2 and 5-HT2A Receptors. Bioorg. Med. Chem. Lett. 13:175-178. (2003).

Newman, A. H. Novel pharmacotherapies for cocaine abuse 1997-2000. Exp. Opin. Ther. Patents. 10(7):1095-1122. (2000).

Robichaud, A. J. et al. Recent Advances in Selective Serotonin Receptor Modulation. Ch. 2. in Ann. Rep. Med. Chem. v. 35. (2000) Raleigh, NC: Academic Press (Elsevier). pp. 11-20.

Zhang, A. et al. Recent advances towards the discovery of dopamine receptor ligands. Expert Opin. Ther. Patents. 16(5):587-630. (2006).

(56) References Cited

OTHER PUBLICATIONS

Allan, G., et al., "One-pot deracemisation of an enol acetate derived from a prochiral cyclohexanone", Tetrahedron Letters, 2001; 42:5959-5962.

Dinh, P., et al., "Catalytic racemisation of alcohols: applications to enzymatic resolution reactions", Tetrahedron Letters, 1996; 37(42):7623-7626.

Francotte, E., "Enantioselective chromatography as a powerful alternative for the preparation of drug enantiomers", Journal of Chromatography A, 2001; 906:379-397.

Maruzen, "The fourth series of experimental chemistry," The Chemical Society of Japan, 1998; 27:426-439.

Adler, L., et al., "Schizophrenia, sensory gating, and nicotinic receptors", Schizophrenia Bulletin, 1998; 24 (2):189-202.

Bastin, R.J., et al., "Salt selection and optimisation procedures for pharmaceutical new chemical entities," Organic Process Research & Development, 2000, 4:427-435.

Birrell, J., et al., "Medial frontal cortex mediates preceptual attentional set shifting in the rat", Journal of Neuroscience, 2000; 20(11):4320-4324.

Bogeso, K.P., et al., "Stereospecific and selective 5-HT2 antagonism is a series of 5-substituted trans-1-piperazino-3-phenylindans," J. Med. Chem., 1993, 36:2761-2770.

Desiraju, G.R., "Cryptic crystallography," Nature Matter, 2002, 1:77-79.

Farde, L., et al., "Positron emission tomographic analysis of central D1 and D2 dopamine receptor occupancy in patients treated with classical neuroleptics and clozapine: relation to extrapyramidal side effects", Archives of General Psychiatry, 1992; 49:538-544.

Green, M. F., et al., "The neurocognitive effects of low-dose haloperidol: a two-year comparison with risperidone", Society of Biological Psychiatry, 2002; 51:972-978.

Harvey, P.D., et al., "Studies of cognitive change in patients with schizophrenia following novel antipsychotic treatment", American Journal Psychiatry, 2001; 158:176-184.

Hertel, R, et al., "Repeated administration of the neurotensin analogue NT69L induces tolerance to its suppressant effect on conditioned avoidance behaviour", Eur. J. Pharmacology, 2002; 439:107-111.

Keefe, R. et al., "The brief assessment of cognition in schizophrenia: reliability, sensitivity, and comparison with a standard neurocognitive battery", Schizophrenia Research, 2004; 68:283-297.

Meltzer, H.Y., et al., "The effects of clozapine, risperidone, and olanzapine on cognitive function in schizophrenia", Schizophrenia Bulletin, 1999; 25(2):233-255.

Mitchell, E.S., et al., "5-HT6 receptors: a novel target for cognitive enhancement", Pharmacology & Therapeutics, 2005; 108:320-33.

Price, S. L. "The computational prediction of pharmaceutical crystal structures and polymorphism," Adv. Drug Delivery Rev. 56:301-19 (2004).

Rodefer, J., et al., "PDE10A inhibition reverses subchronic PCP-induced deficits in attentional set-shifting in rats", European J. Neuroscience, 2005; 21:1070-1076.

Chemical Abstract Society No. 94800-10-9.

Chemical Abstract Society No. 25086-89-9.

* cited by examiner

PROCESS FOR MAKING TRANS-1-((1R,3S)-6-CHLORO-3-PHENYLINDAN-1-YL)-3,3-DIMETHYLPIPERAZINE

CROSS-REFERENCE TO RELATED APPLICATION

The present application is a U.S. National Stage Application of International Application No. PCT/DK2006/000086 (International Publication No. WO/2006/086984), filed Feb. 14, 2006, which claims the benefit of Danish Patent Application Serial No. DK PA 2005 00237 and U.S. Provisional Patent Application Ser. No. 60/653,428, both of which were filed Feb. 16, 2005. Each of these applications is herein incorporated by reference in its entirety.

The present invention relates to a process for making trans-1-((1R,3S)-6-chloro-3-phenylindan-1-yl)-3,3-dimethylpiperazine (Compound I) and salts thereof.

BACKGROUND OF THE INVENTION

The compound, which is the subject of the present invention (Compound I, trans-1-((1R,3S)-6-chloro-3-phenylindan-1-yl)-3,3-dimethylpiperazine) has the general formula (I).

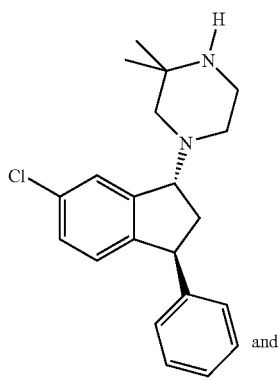

and

Compound I and salts thereof, including a fumarate and maleate salt thereof, and the medical uses thereof, e.g. in schizophrenia or other diseases involving psychotic symptoms, are described in PCT/DK04/000546 (WO05/016901).

As described in PCT/DK04/000546 the inventors have found that Compound I displays high affinity for dopamine (DA) D1 receptors, DA D2 receptors and for alfa1 adrenoceptors. Furthermore, Compound I was found to be an antagonist at dopamine D1 and D2 receptors, and at serotonin 5-HT2a receptors. As further described in PCT/DK04/000546, Compound I is a relatively weak inhibitor of CYP2D6 (i.e. reduced potential for drug to drug interaction) and has a relatively low effect on the QT interval in a rabbit model (i.e. reduced potential for introducing drug-induced QT interval prolongation and appearance of fatal cardiac arrhythmias, torsade de pointes (TdP), in humans). Additionally, the $5\text{-}HT_2$ antagonistic activity of Compound I suggests that Compound I may have a relatively low risk of extrapyramidal side effects.

The properties outlined above, e.g. binding assays (including alfa-1, DA D1 or D2 receptors), efficacy assays (including DA D1 or D2, or serotonin $5\text{-}HT_{2A}$ receptors), CYP2D6 inhibition and QT-interval may be determined as described in PCT/DK04/000546, cf. in particular the "Example" section page 19-24 in the application text as filed for PCT/DK04/000546.

Further, the inventors have found that Compound I did not induce dystonia when tested in pigs sensitized to haloperidol, indicating that Compound I does not possess EPS (extrapyramidal symptoms) response/liability in humans.

PCT/DK04/000546 describes the following medical uses of Compound I: a disease in the central nervous system, including psychosis, in particular schizophrenia (e.g. positive, negative, and/or depressive symptoms) or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. mania in bipolar disorder. Also described is the use of Compound I for treatment of anxiety disorders, affective disorders including depression, sleep disturbances, migraine, neuroleptic-induced parkinsonism, or cocaine abuse, nicotine abuse, alcohol abuse and other abuse disorders.

As indicated in PCT/DK04/000546 a group of compounds structurally related to Compound I, i.e. trans isomers of 3-aryl-1-(1-piperazinyl)indanes substituted in the 2- and/or 3-position of the piperazine ring, has been described in EP 638 073; Bøgesø et al. in J. Med. Chem., 1995, 38, 4380-4392 and Klaus P. Bøgesø in "Drug Hunting, the Medicinal Chemistry of 1-Piperazino-3-phenylindans and Related Compounds", 1998, *ISBN* 87-88085-10-4I. For example, an enantiomeric pure compound corresponding to formula (I) but differing in that it has an N-methyl group instead of an N-hydrogen on the piperazine has been disclosed in Bøgesø et al. in J. Med. Chem., 1995, 38, 4380-4392, see table 5, compound (−)-38.

None of the above references apart from PCT/DK04/000546 disclose the specific enantiomeric form above (Compound I) or medical use thereof. The trans isomer in the form of the racemate of Compound I is only indirectly disclosed as an intermediate in the synthesis of compound 38 in Bøgesø et al. in J. Med. Chem., 1995, 38, 4380-4392 while medical use of Compound I or its corresponding racemate is not described. Compound I as an intermediate is disclosed in PCT/DK04/000545 (WO05/016900).

DETAILED DESCRIPTION OF THE INVENTION

The present invention in one aspect relates to a new process for the preparation of Compound I wherein the chirality is introduced earlier in the manufacturing process as compared to the process described in PCT/DK04/000546. The introduction of the chirality one step earlier is an advantage because the following step becomes more efficient in terms of e.g. volume yield, and consumption of reagents and solvents and production of less waste. In PCT/DK04/000546, the chirality is introduced by resolving the racemic intermediate V below, either enzymatically or by chiral HPLC. The present inventors have now developed a route of synthesis in which the enantiomer of formula (I) is obtained via a sequence starting from enantiomeric pure IV, i.e. Compound IVa ((S)-6-chloro-3-phenylindan-1-one, see below). Thus, in this process, the intermediate of formula IV is resolved, e.g. by chiral chromatography, to obtain the enantiomer of formula IVa.

Furthermore, the present inventors have developed a method for the racemisation of the undesired enantiomer (Compound IVb, see below), which then can be reused in the resolution. This has a tremendous impact on the efficiency of the whole synthesis, as the efficiency of the steps before the resolution is increased as well as the subsequent steps.

Accordingly, the enantiomer of formula (I) may be obtained by a process involving the following steps:

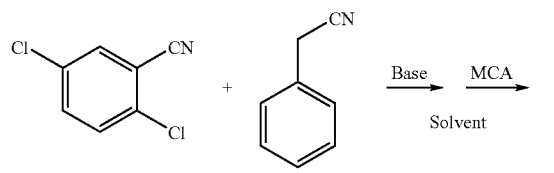

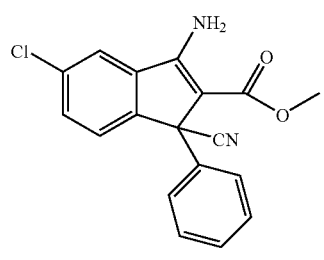

(II)

Benzyl cyanide is reacted with 2,5-dichlorobenzonitril in the presence of a base, suitably potassium tert-butoxide (t-BuOK) in a suitable solvent such as 1,2-dimethoxyethane (DME), further reaction with methyl chloro acetate (MCA) leads to spontaneous ring closure and one pot formation of the compound of formula (II).

The compound of formula (II) is then subjected to acidic hydrolysis to form a compound of formula (III), suitably by heating in a mixture of acetic acid, sulphuric acid and water, and thereafter decarboxylation, e.g., by heating the compound of formula (III) in a suitable solvent, such as toluene with triethyl amine or N-methyl pyrrolidin-2-one (NMP), to form a compound of formula (IV).

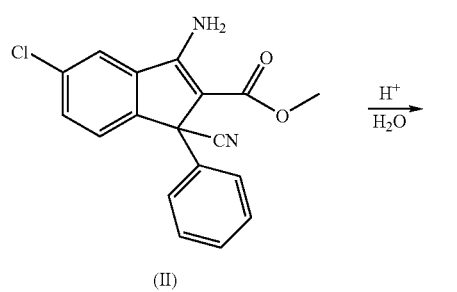

(II)

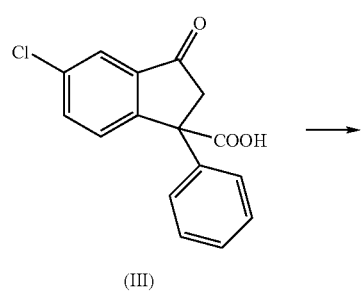

(III)

(IV)

The compound of formula (IV) is resolved to achieve the desired enantiomer (formula IVa) for the further synthesis of Compound I, and the undesired enantiomer (formula IVb) which may be subjected to racemisation and recycling:

(IVa)

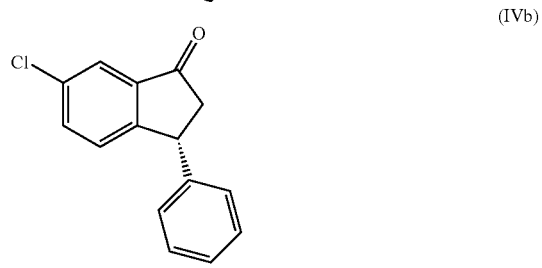

(IVb)

The resolution of IV may, e.g., be performed using chiral chromatography, preferable liquid chromatography, or sub- or supercritical fluid chromatography.

Chiral liquid chromatography may, e.g., be performed on a chiral stationary phase, suitably on a column of silica gel with an immobilized chiral polymer, or preferably on a column of silica gel coated with a chiral polymer, e.g. a modified cellulose, or a modified amylose, such as amylose tris [(S)-α-methylbenzylcarbamate], preferably a column of silica gel coated with amylose tris [(S)-α-methylbenzylcarbamate].

A suitable solvent is used for the chiral liquid chromatography, such as, e.g. an alcohol (preferably a $C_{1-4}$-alcohol), a nitrile, an ether, or an alkane (preferably a $C_{5-10}$-alkane), or mixtures thereof, suitably ethanol, methanol, iso-propanol, acetonitrile, methyl tert-butyl ether or n-heptane or mixtures thereof, preferably ethanol or n-heptane or a mixture thereof. Acidic or basic modifiers can be added to the eluent, e.g. formic acid, acetic acid, trifluoroacetic acid, triethylamine, or N,N-diethylamine.

Sub- or supercritical fluid chromatography may, e.g., be performed on a chiral stationary phase, suitably on a column of silica gel with an immobilized chiral polymer, or on a column of silica gel coated with a chiral polymer, e.g. a modified amylose, such as amylose tris [(S)-α-methylbenzyl-carbamate], or preferably amylose tris (3,5-dimethylphenyl-carbamate), most preferably amylose tris (3,5-dimethylphenylcarbamate) coated on silica gel, or a modified cellulose, such as cellulose tris (4-methylbenzoate), or preferable cellulose tris (3,5-dimethylphenylcarbamate), most preferably cellulose tris (3,5-dimethylphenylcarbamate) coated on silica gel. Other types of chiral stationary phases may be used, e.g. the Pirkle type columns, suitable on a column of silica gel with covalently bonded 3,5-dinitrobenzoyl tetrahydrophenanthrene amine.

Sub- or supercritical carbon dioxide, suitable supercritical carbon dioxide, containing a modifier may be used as eluent for the sub- or supercritical fluid chromatography. The modifier is selected from the lower alcohols such as methanol, ethanol, propanol and isopropanol, or e.g. acetonitril may be used. An amine, such as diethylamine, optionally 0.1% diethylamine, triethylamine, propylamine, and dimethyl isopropyl amine, and optionally an acid, such as formic acid, acetic acid and trifluoroacetic acid may be added.

In a further embodiment of the invention the modifier is selected from the lower alcohols such as methanol, ethanol, propanol and isopropanol, or e.g. acetonitril may be used, as long as the modifier is compatible with the column.

The chiral chromatography can be scaled up using suitable technologies, e.g. simulated moving bed technology (SMB), or sub- or supercritical fluid technology (cf G. B. Cox (ed.) *Preparative Enantioselective Chromatography*, Blackwell Publishing Ltd., Oxford, UK, 2005).

The compound of formula (IVa) is then reduced e.g. with a complex metal hydride, such as borohydride, suitably with sodium borohydride (NaBH$_4$) or such as lithium aluminiumhydride, in a solvent, such as an alcohol (e.g. a C$_{1-5}$-alcohol), e.g. ethanol or iso-propanol, and preferably at a temperature in the range of about −30° to +30° C., e.g. below 30° C., below 20° C., below 10° C., or preferably below 5° C., to form a compound of formula (Va) with cis configuration:

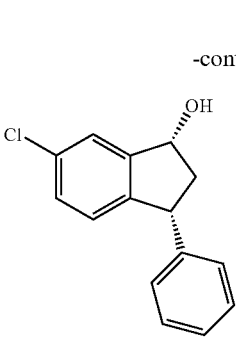

(V)

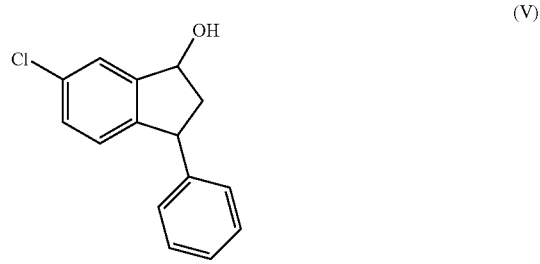

(Va)

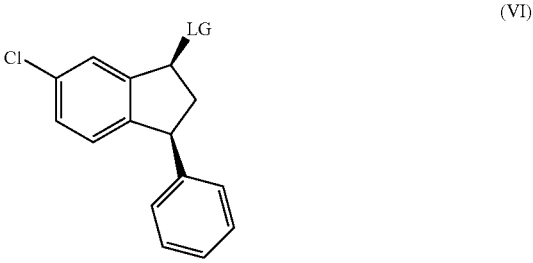

(Vb)

The alcohol group of the cis-alcohol of formula (Va) is converted to a suitable leaving group, such as, e.g., a halogen, e.g. Cl or Br, preferably Cl, or a sulphonate, e.g. mesylate (methansulfonylate) or tosylate (4-toluenesulfonylate), suitably by reaction with an agent, such as thionyl chloride, mesyl (methansulfonyl) chloride or tosyl (4-toluenesulfonyl) chloride, in an inert solvent, e.g. an ether, suitably tetrahydrofuran. The resulting compound has formula (VI), where LG is the leaving group:

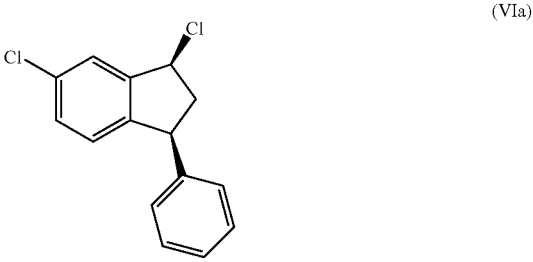 [SMILES: Clc1ccc2c(c1)[C@@H](Cl)C[C@H]2c1ccccc1]

(VI)

In a preferred embodiment, LG is Cl, i.e. the cis-chloride of formula (VIa):

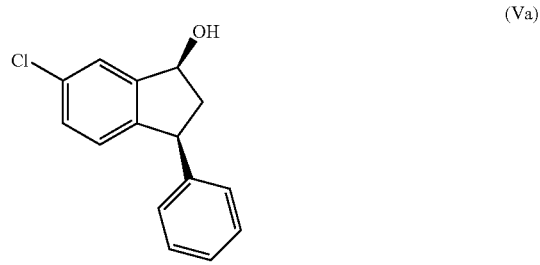 [SMILES: O[C@H]1C[C@@H](c2ccccc2)c2ccc(Cl)cc21]

(VIa)

Compound VI, e.g. with LG as chloro, is then reacted with 2,2-dimethylpiperazine in a suitable solvent, e.g. a ketone such as, e.g., methyl isobutyl ketone or methyl ethyl ketone, preferably methyl isobutyl ketone in the presence of a base, such as e.g., potassium carbonate, to obtain Compound I.

Alternatively, the piperazine part of the molecule may be introduced by reacting Compound VI with a compound of formula (VII) below, where PG is a protecting group, such as, but not restricted to, e.g. phenylmethoxycarbonyl (often called Cbz or Z), tert-butyloxycarbonyl lo (often called BOC), ethoxycarbonyl, or benzyl, thereby obtaining the compound of formula (VIII) below. Compound VIII is subsequently deprotected to afford Compound I.

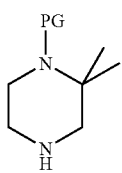

(VII)

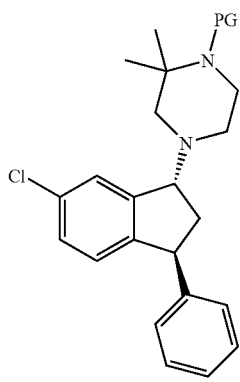

(VIII)

A further embodiment of the invention relates to a method for the manufacturing of a compound [Compound IX: 4-((1R, 3S)-6-chloro-3-phenylindan-1-yl)-1,2,2-trimethylpiperazine] having the following formula (IX) or a salt thereof:

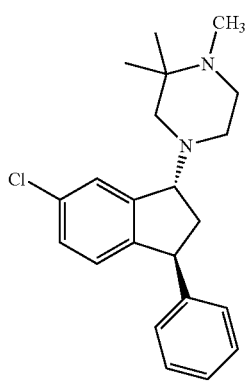

(IX)

which method comprises:

(i) manufacturing Compound I by a method of the present invention, i.e. in particular from Compound IVa; and (ii) converting Compound I into Compound IX, preferably by methylating the secondary amine functionality, suitably by reductive alkylation using suitable agents, such as, e.g., formaldehyde, paraformaldehyde, trioxane, or diethoxy methane (DEM).

The term reductive alkylation refers to the above-mentioned reagents in combination with a reductive agent, such as formic acid.

Thus, further embodiment of the invention relates to the methods as described herein for the manufacturing of Compound I, wherein Compound I is "replaced" by Compound IX.

Compound IX is described generically in EP 638 073 while the enantiomer of formula (IX) has been described by Bøgesø et al. in J. Med. Chem., 1995, 38, page 4380-4392, in the form of the fumarate salt, see table 5, compound (−)-38. Compound IX and a method for manufacturing Compound IX from Compound I, and salts of Compound IX (in particular a crystalline succinate salt and a crystalline malonate salt) are further described in PCT/DK2004/00545.

As indicated above the invention also relates to a method for the manufacturing of Compound I or Compound IX as described herein wherein Compound IVb is recycled such that it can be used for the synthesis of Compound I or Compound IX, respectively, see also the illustration below.

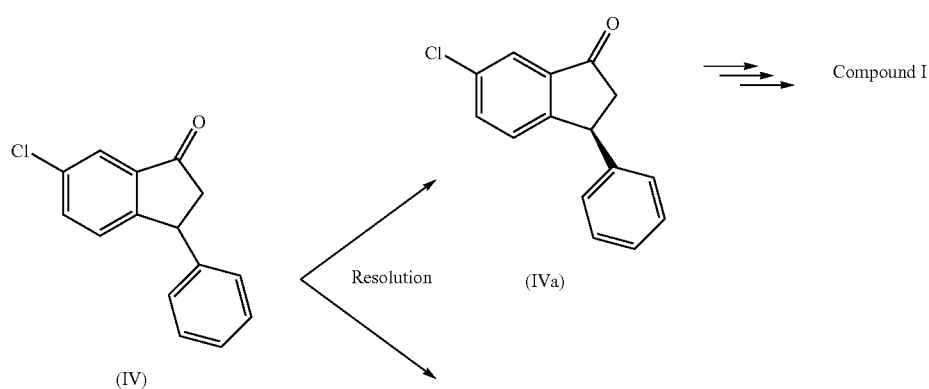

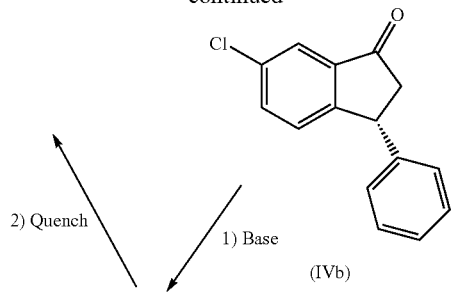

(IVb)

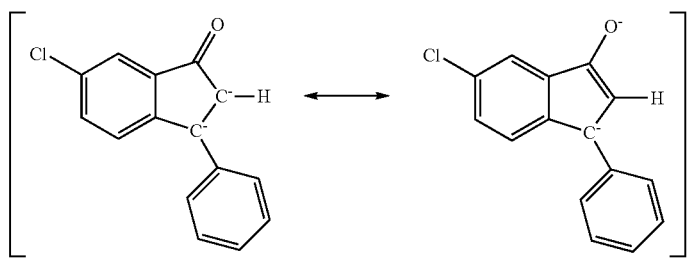

Surprisingly, the racemisation of compound IVb can be achieved using different types of bases, e.g. an amide, preferably a dialkylamide, e.g. but not limited to lithium diethylamide, lithium diisopropylamide, lithium tetramethylpiperidide, suitable lithium diisopropylamide (LDA), or a metal bis-silylamide, e.g. alkali bis(trimethylsilyl)amide, or an metal alkoxide, e.g. but not limited to metal methoxide, metal ethoxide, metal tert-butoxide, suitably alkali alkoxide, preferably potassium alkoxide, must preferably potassium tert-butoxide, or an alkyl metal, suitable an alkyl lithium, preferably butyl lithium or tert-butyl lithium. After quenching the reaction mixture, the racemic ketone IV can be isolated.

The racemisation can be achieved using two different bases as well; again, different types of non nucleophillic bases can by used as "the former base" (base 1), e.g. an amide, preferably a dialkylamide, e.g. but not limited to lithium diethylamide, lithium diisopropylamide, lithium tetramethylpiperidide, suitable lithium diisopropylamide (LDA), or a metal bis-silylamide, e.g. lithium bis-silylamide, suitably lithium bis(trimethylsilyl)amide, or an metal alkoxide, e.g. but not limited to metal methoxide, metal ethoxide, metal tert-butoxide, suitably alkali alkoxide, preferably lithium alkoxide, must preferably lithium tert-butoxide. After the former base (base 1) have been mixed with the ketone, "the latter base" (base 2) is added. As with the former base, different types of bases can be used; e.g. an amide, preferably a dialkylamide, e.g. but not limited to lithium diethylamide, lithium diisopropylamide, lithium tetramethylpiperidide, suitable lithium diisopropylamide (LDA), or a metal bis-silylamide, e.g. alkali bis(trimethylsilyl)amide, or an metal alkoxide, e.g. but not limited to metal methoxide, metal ethoxide, metal tert-butoxide, suitably alkali alkoxide, preferably potassium alkoxide, must preferably potassium tert-butoxide, or an allyl metal, suitable an alkyl lithium, preferably butyl lithium or tert-butyl lithium.

Furthermore, racemisation can be obtained using two or more different bases by adding them all from the very start, preferable by adding two different bases from the very start.

In a further embodiment of the invention the racemisation can achieved by using a nucleophillic base.

Alternatively, the racemic alcohol V can be resolved by chiral chromatography as described in PCT/DK04/000546, to obtain Va for the synthesis of Compound I, and Vb, which can be racemerised and reused in the resolution as indicated in the figure below. The racemisation of Vb is obtained by oxidation of Vb to IVb, e.g. by using pyridinium chlorochromate (PCC), racemisation of IVb to IV as described above, and then reduction of IV to V in the usual way, as described above.

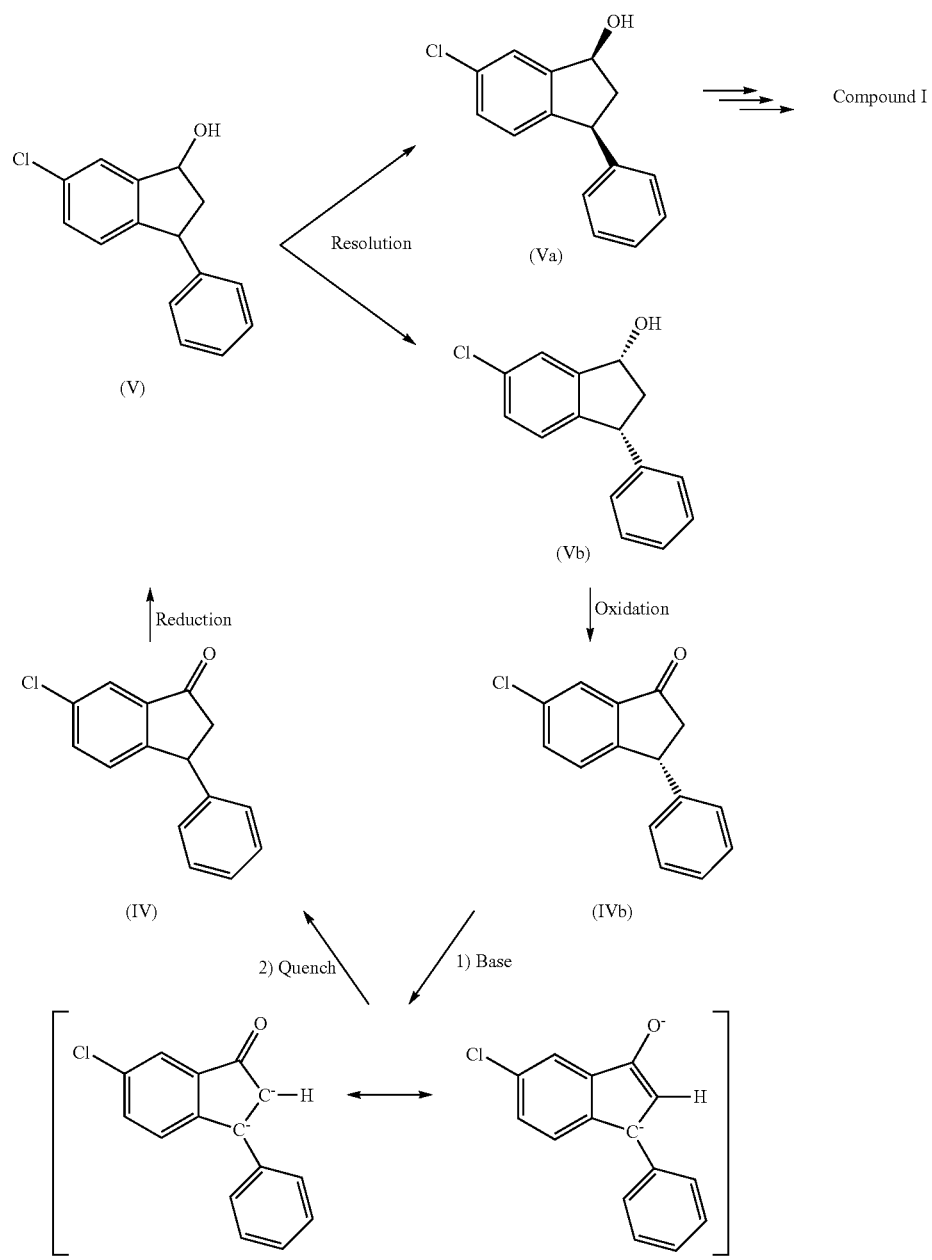

When studying the racemisation on a 10 g scale, an impurity as a by product can be detected by LC-MS (liquid chromatography—mass spectroscopy); analytic data suggest that the impurity is a dimer of IV and/or the enantiomers IVa and IVb. The analytical data furthermore indicates, that the dimer can eliminate water, depending on the work up procedure. Laborious work has shown, that the formation of the dimer can be suppressed appreciably by carefully selecting the conditions for the racemisation, and the content of the dimer in the product can by further reduced by recrystallising the product from a suitably lo solvent, e.g. an alcohol, preferably ethanol or 2-propanol.

During the synthesis of Compound I some cis diastereoisomer of Compound I (i.e. 1-((1S,3S)-6-chloro-3-phenylindan- 1-yl)-3,3-dimethylpiperazine) may be formed as an impurity in the final product. This impurity is due mainly to the formation of some of the trans form of (VI) (e.g. (1S,3R)-3,5-dichloro-1-phenylindan when LG is Cl) in the step where Compound VI is formed. Therefore, the impurity can be minimized by crystallisation of the desired cis form of Compound VI, from the mixture of trans and cis (VI); in the case where LG is Cl in Compound VI this can be done by stirring the mixture with a suitable solvent, e.g. an alkane ($C_{5-10}$-alkane), such as heptane, whereby the desired cis form of VI precipitates and the undesired trans form of Compound VI goes into solution. The desired cis form of Compound VI (e.g. when LG is Cl) is isolated, e.g., by filtration, and preferably washed with the solvent in question and dried.

The cis form of Compound I may also be removed by precipitation of a suitable salt of Compound I, e.g. a hydrochloride salt or a salt of an organic acid, such as an organic diacid, suitably a fumarate salt or a maleate salt of the compound of formula (I), optionally followed by one or more re-crystallisations e.g. as described in PCT/DK2004/000546.

The cis form of Compound I may also be removed by isolating Compound 1 as the free base from a suitable solvent.

The invention in further aspects also relates to the intermediates as described herein for the synthesis of the Compound I, in particular the intermediates IVa and IVb. In this context is understood when specifying the stereoisomeric form, that the stereoisomer is the main constituent. In particular, when specifying the enantiomeric form, then the compound has an enantiomeric excess of the enantiomer in question.

Accordingly, one embodiment of the invention relates to the compound of formula (IVa), preferably having an enantiomeric excess of at least 60% (60% enantiomeric excess means that the ratio of Compound IVa to its enantiomer is 80:20 in the mixture in question), at least 70%, at least 80%, at least 85%, at least 90%, at least 96%, preferably at least 98%. One embodiment relates to substantially pure Compound IVa.

A further embodiment of the invention relates to the compound of formula (IVb), preferably having an enantiomeric excess of at least 60%.

The invention in a further aspect relates to Compound I or a salt thereof (e.g. a HCl, a fumarate or a maleate salt thereof) obtained by a method of the invention, and the medical use thereof, in particular for the medical indication as disclosed herein, e.g. as an antipsycotic, such as for schizophrenia. Also within the invention are a pharmaceutical composition of Compound I or salt thereof obtained by a method of the invention.

In the present context, in particular for the pharmaceutical uses of Compound I, it is understood that when specifying the enantiomer form as done in formula (I), then the compound is preferably relatively stereochemically pure, preferably the enantiomeric excess is at least 60%, at least 70%, and more preferably at least 80% (80% enantiomeric excess means that the ratio of I to its enantiomer is 90:10 in the mixture in question) at least 90%, at least 96%, or preferably at least 98%. In a preferred embodiment, the diastereomeric excess of Compound I is at least 90% (90% diastereomeric purity means the ratio of Compound I to cis-1-((IS,3S)-6-chloro-3-phenylindan-1-yl)-3,3-dimethylpiperazine is 95:5), at least 95%, at least 97%, or at least 98%.

Accordingly, the process of the invention may comprise a step whereby Compound I or a salt thereof is formulated into a pharmaceutical composition. The compound, salt or composition of Compound I may be administered in any suitable way e.g. orally, buccal, sublingual or parenterally, and the compound or salt may be presented in any suitable form for such administration, e.g. in the form of tablets, capsules, powders, syrups or solutions or dispersions for injection. In one embodiment, the compound or salt of the invention are administered in the form of a solid pharmaceutical entity, suitably as a tablet or a capsule.

Methods for the preparation of solid pharmaceutical preparations are well known in the art. Tablets may thus be prepared by mixing the active ingredient with ordinary adjuvants, fillers and diluents and subsequently compressing the mixture in a convenient tabletting machine. Examples of adjuvants, fillers and diluents comprise corn starch, lactose, talcum, magnesium stearate, gelatine, lactose, gums, and the like. Any other adjuvant or additive such as colourings, aroma, preservatives, etc. may also be used provided that they are compatible with the active ingredients.

Solutions for injections may be prepared by dissolving a salt of the invention and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, solubilising agents etc.

The daily dose of the compound of formula (I) above, calculated as the free base, is suitably between 1.0 and 160 mg/day, more suitable between 1 and 100 mg, e.g. preferably between 2 and 55 mg.

The term "treatment" as used herein in connection with a disease or disorders includes also prevention as the case may be.

The invention will be illustrated in the following non-limiting examples.

EXAMPLES

Analytical Methods

The enantiomeric excess of compounds (IV), (IVa), and (IVb) is determined by supercritical fluid chromatography using a Gilson SF3 Supercritical Fluid Chromatography System, detection is performed using a Gilson U/VIS-831 detector at 254 nm. Either a CHIRALPAK® AD-H column, 0.46 cm ID×25 cm L, at room temperature is used under the following conditions: Eluent: Ethanol with 0.1% diethylamine is used at modifier (30%), the flow is 3 ml/min, and the pressure is 200 bar. The retention time of the two enantiomers are 2.36 min. (IVa) and 2.99 min. (IVb). Or a CHIRALCEL® OD-H column, 0.46 cm ID×25 cm L, at room temperature is used under the following conditions: Eluent: Ethanol (30%) is used as modifier, the flow is 4 ml/min, and the pressure is 200 bar.

The enantiomeric excess of compound (Va) in Example 8 is determined by supercritical fluid chromatography using a Gilson SF3 Supercritical Fluid Chromatography System with a CHIRALPAK® AD-H column, 0.46 cm ID×25cm L, at room temperature. Eluent: Ethanol with 0.1% diethylamine is used at modifier (30%), the flow is 3 ml/min, and the pressure is 200 bar. Detection is performed using a Gilson UV/VIS-831 detector at 254 nm. The retention time of the two enantiomers are 2.41 min. (Va) and 3.06 min. (Vb). The enantiomeric excess of compound (Va) in Example 1a is determined by chiral HPLC using a CHIRALCEL® OD column, 0.46cm ID×25 cm L, 10 μm at 40° C. n-Hexan/ethanol 95:5 (vol/vol) is used as mobile phase at a flow rate of 1.0 ml/min, detection is performed using a UV detector at 220 nm.

The enantiomeric excess of compound (I) is determined by fused silica capillary electrophoresis (CE) using the following conditions: Capillar: 50 μm ID×48.5 cm L, run buffer: 1.25mM β cyclo dextrin in 25 mM sodium dihydrogen phosphate, pH 1.5, voltage: 16 kV, temperature: 22° C., injection: 40 mbar for 4 seconds, detection: column diode array detection at 195 nm, sample concentration: 500 μg/ml. In this system, Compound I has a retention time of approximately 10 min, and the other enantiomer has a retention time of approximately 11 min.

The enantiomeric excess of compound (IX) is determined by fused silica capillary electrophoresis (CE) using the following conditions: Capillar: 50 μm ID×64.5 cm L, run buffer: 3.0 mM β cyclo dextrin and 10 mM hydroxypropyl β cyclo dextrin in 50 mM sodium dihydrogen phosphate, pH 1.5, voltage: 15 kV, temperature: 22° C., injection: 40 mbar for 4 seconds, detection: column diode array detection at 192 nm, sample concentration: 100 μg/ml. In this system, Compound IX has a retention time of approximately 47 min, and the enantiomer has a retention time of approximately 46 min. The other two diastereoisomers 4-((1R,3R)-6-Chloro-3-phenyl-indan-1-yl)-1,2,2-trimethyl-piperazine and 4-((1S,3S)-6-Chloro-3-phenyl-indan-1-yl)-1,2,2-trimethyl-piperazine have retention times of approximately 49 min. and 52 min. respectively.

$^1$H NMR spectra are recorded at 500.13 MHz on a Bruker Avance AV-500 instrument or a Bruker Avance DRX500 instrument, or at 250.13 MHz on a Bruker Avance DPX-250 instrument or a Bruker AC 250 instrument. Chloroform (99.8% D) or dimethyl sulfoxide (99.8% D) is used as solvents, and tetramethylsilane (TMS) is used as internal reference standard.

The cis/trans ratio of Compound I and IX is determined using $^1$H NMR as described in Bøgesø et al., *J. Med. Chem.* 1995, 38, 4380-4392 (page 4388, right column). The cis/trans ratio of compound VIa is determined by $^1$H NMR in DMSO-$d_6$, using the integrals of the signal at 5.6 ppm for the cis isomer and the signal at 5.75 ppm for the trans isomer, or by $^1$H NMR in chloroform, using the integrals of the signal at 5.3 ppm for the cis isomer and the signal at 5.5 ppm for the trans isomer. Generally, a content of approximately 1% of the undesired isomer can be detected by NMR.

The Melting points are measured using Differential Scanning Calorimetry (DSC). The equipment is a TA-Instruments DSC-Q1000 or a TA-instruments DSC-2920 calibrated at 5°/min to give the melting point as onset value. About 2 mg of sample is heated 5°/min in a loosely closed pan under nitrogen flow.

The elemental analysis is performed using a Vario El analysator from Elementar build to measure C, H, and N content. The value given is the mean of two determinations using approximately 4 mg each.

The optical rotation is measured using a Perkin Elmer model 241 polarimeter, the concentration is 1% in methanol unless otherwise stated.

LC-MS is performed using a Waters Symmetry C-18 column, 0.46 cm ID×3 cm L, 3.5 µm, at 60° C. The eluent is a gradient of (A) water with 0.05% trifluoroacetic acid and (B) acetonitril with 5% water and 0.035% trifluroacetic acid, going from 90% A and 10% B to 100% B in 2 minutes; flow 3 ml/min. Detection is performed using a Shimadzu detector at 254 nm. The mass spectrum is recorded by a Sciex API300 mass spectrometer.

Synthesis

Synthesis of Key Starting Materials

Compound V is synthesised from IV by reduction with sodium borohydride (NaBH$_4$) adapting a method described in Bøgesø *J. Med. Chem.* 1983, 26, 935, using ethanol as solvent, and performing the reaction at approximately 0° C. Both compounds are described in Bøgesø et al. *J. Med. Chem.* 1995, 38, 4380-4392. Compound IV is synthesised from II using the general procedures described in Sommer et al., *J. Org. Chem.* 1990, 55, 4822, which also describes II and the synthesis thereof.

Example 0a

Synthesis of (S)-6-chloro-3-phenylindan-1-one (IVa) and (R)-6-chloro-3-phenylindan-1-one (IVb) by use of Chiral Chromatography Racemic 6-chloro-3-phenylindan-1-one (IV) is resolved by preparative chromatography, using a CHIRALPAK! AS-V column. A mixture of n-heptane, ethanol and N,N-diethylamine is used as mobile phase, detection is performed using a UV detector at 220 nm. The racemic ketone (IV) is injected as a solution in the eluent; suitable volumes of the solution is injected with suitable intervals. All the fractions, which contain compound (IVa) with more than 98% enantiomeric excess, are combined and evaporated to dryness using a rotary evaporator. All fractions, which contain compound (IVb) or mixtures of compounds (IVa) and (IVb) are combined and evaporated to dryness using a rotary evaporator.

Example 0b

Synthesis of Enantiomeric Pure (R)-6-chloro-3-phenylindan-1-one (IVb) by Oxidation of (1R,3R)-6-chloro-3-phenylindan-1-ol (Vb)

(1R,3R)-6-chloro-3-phenylindan-1-ol (Vb) isolated as in example 1a (20g) is dissolved in dichloromethane (400 ml) and pyridinium chlorochromate (PCC) (26.5 g) is added. The mixture is stirred for 1½ hour at room temperature. The mixture is filtered, and the oily residue in the reaction vessel is washed with dichloromethane. The combined organic fractions are evaporated to dryness on a rotary evaporator, giving a black oil (25 g). Ethyl acetate (200 ml) and sodium hydroxide (2M in water, 200 ml) are added. The phases are separated, and the water phase is extracted twice with ethyl acetate (200 ml). The combined organic phases are washed three times with sodium hydroxide (2M in water, 100 ml), twice with water (100 ml), and once with brine (100 ml), and finally dried with sodium sulphate. Evaporation to dryness followed by drying in a vacuum oven at 40° C. gives 15 grams of crystals. $[\alpha]_D^{20}$ −61° (c=1.0, methanol). 90% ee according to the chiral analysis.

Example 0c

Racemisation of (R)-6-chloro-3-phenylindan-1-one (IVb)

Diisopropyl amine (5.1 ml) is dissolved in dry tetrahydrofuran (THF) (50 ml) and the solution is stirred under nitrogen with cooling in an acetone/dry ice bath. Butyl lithium (1.6 M in hexane, 22.6 ml) is added slowly, where after the cooling bath is replaced with an ice/water bath. After stirring for 1½ hour, (R)-6-chloro-3-phenylindan-1-one (IVb) synthesised in example 0b (7.05 g, 90% ee) dissolved in dry THF (60 ml) is added over 30 minutes, and stirring on the cooling bath is continued for 17 minutes. Then potassium tert-butoxide (1.0 M in THF, 28.8 ml) is added over 17 minutes, and then stirring is continued for another two hours on the ice/water bath. The reaction mixture is quenched with hydrochloric acid (4 M, 50 ml), and then THF is removed from the mixture on the rotary evaporator. Water (200 ml) and diethyl ether (350 ml) are added, and the phases are separated. The water phase is extracted twice with diethyl ether (200 ml, then 100 ml). The combined organic phases are washed twice with water (100 ml), once with brine (100 ml), and dried with sodium sulphate. Evaporation to dryness on a rotary evaporator, followed by drying in a vacuum oven at 40° C., gives 6.70 g of a red solid. $[\alpha]_D^{20}$ −2.34° (c=1.0, methanol). The product has an enantiomeric excess of 2% according to the chiral analysis, and contains 6% of the by product (see body text) according to HPLC. The raw product (4.99 g) is recrystallised from absolute ethanol (40 ml), giving 3.71 g of a red solid. $[\alpha]_D^{20}$ −0.84° (c=1.0, methanol). Contains 2.6% of the by product (see body text) according to HPLC.

Example 1a

Synthesis of (1S,3S)-6-chloro-3-phenylindan-1-ol (Va) and (1R,3R)-6-chloro-3-phenyl-indan-1-ol (Vb) by use of Chiral Chromatography Racemic cis-6-chloro-3-phenylindan-1-ol (V) (492 grams) is resolved by preparative chromatography, using a CHIRAL-PAK® AD column, 10 cm ID×50 cm L, 10 µm at 40° C. Methanol is used as mobile phase at a flow rate of 190 ml/min, detection is performed using a UV detector at 287 nm. The racemic alcohol (V) is injected as a 50,000 ppm solution in methanol; 90 ml is injected with intervals of 28 min. All the fractions, which contain compound (Va) with more than 98% enantiomeric excess, are combined and evaporated to dryness using a rotary evaporator, followed by drying "in vacuo" at 40° C. Yield 220 grams as a solid. Elemental analysis and NMR conform to the structure, the enantiomeric excess is higher than 98% according to chiral HPLC, $[\alpha]_D^{20}$ +44.5° (c=1.0, methanol). Likewise, the fractions, which contain compound (Vb) are combined and evaporated to dryness, giving 214 g of (Vb).

Example 1b

Synthesis of (1S,3S)-6-chloro-3-phenylindan-1-ol (Va) by Reduction of Enantiomeric Pure (IVa)

(S)-6-chloro-3-phenylindan-1-one (IVa) can by reduced with sodium borohydride adapting a method described in Bøgesø *J. Med. Chem.* 1983, 26, 935, using ethanol as solvent and performing the reaction at approximately 0° C., giving compound (Va).

Example 2

Synthesis of (1S,3S)-3,5-dichloro-1-phenylindan (VI, LG=Cl)

Cis-(1S,3S)-6-chloro-3-phenylindan-1-ol (Va) (204 grams) obtained as described in Example 1a is dissolved in THF (1500 ml) and cooled to −5° C. Thionyl chloride (119 grams) is added drop wise as a solution in THF (500 ml) over a period of 1 h. The mixture is stirred at room temperature over night. Ice (100 g) is added to the reaction mixture. When the ice has melted the water phase (A) and the organic phase (B) are separated, and the organic phase B is washed twice with saturated sodium bicarbonate (200 ml). The sodium bicarbonate phases are combined with water phase A, adjusted to pH 9 with sodium hydroxide (28%), and used to wash the organic phase B once again. The resulting water phase (C) and the organic phase B are separated, and the water phase C is extracted with ethyl acetate. The ethyl acetate phase is combined with the organic phase B, dried with magnesium sulphate, and evaporated to dryness using a rotary evaporator, giving the title compound as an oil. Yield 240 grams, which is used directly in the example 5. Cis/trans ratio 77:23 according to NMR.

Example 3

Synthesis of 3,3-dimethylpiperazin-2-one

Potassium carbonate (390 grams) and ethylene diamine (1001 grams) are stirred with toluene (1.50 l). A solution of ethyl 2-bromoisobutyrate (500 grams) in toluene (750 ml) is added. The suspension is heated to reflux over night, and filtered. The filter cake is washed with toluene (500 ml). The combined filtrates (volume 4.0 l) are heated on a water bath and distilled at 0.3 atm. using a Claisen apparatus; first 1200 ml distillate is collected at 35° C. (the temperature in the mixture is 75° C.). More toluene is added (600 ml), and another 1200 ml distillate is collected at 76° C. (the temperature in the mixture is 80° C.). Toluene (750 ml) is added again, and 1100 ml of distillate is collected at 66° C. (temperature in the mixture 71° C.). The mixture is stirred on an ice bath and seeded, whereby the product precipitates. The product is isolated by filtration, washed with toluene, and dried over night in a vacuum oven at 50° C. Yield 171 g (52%) of 3,3-dimethylpiperazin-2-one. NMR consistent with structure.

Example 4

Synthesis of 2,2-dimethylpiperazine

A mixture of 3,3-dimethylpiperazin-2-one (8.28 kg, 64.6 mol) and tetrahydrofuran (THF) (60 kg) is heated to 50-60° C., giving a slightly unclear solution. THF (50 kg) is stirred under nitrogen, and LiAlH$_4$ (250 g, in a soluble plastic bag) is added, which gives a slow evolution of gas. After gas evolution has ceased, more LiAlH$_4$ is added (a total of 3.0 kg, 79.1 mol, is used), and the temperature rises from 22° C. to 50° C. because of an exotherm. The solution of 3,3-dimethylpiperazin-2-one is added slowly over 2 hours at 41-59° C. The suspension is stirred for another hour at 59° C. (jacket temperature 60° C.). The mixture is cooled, and water (3 l) is added over two hours, keeping the temperature below 25° C. (it is necessary to cool with a jacket temperature of 0° C.). Then sodium hydroxide (15%, 3.50 kg) is added over 20 minutes at 23° C., cooling necessary. More water (9 l) is added over half an hour (cooling necessary), and the mixture is stirred over night under nitrogen. Filter agent Celit (4 kg) is added, and the mixture is filtered. The filter cake is washed with THF (40 kg). The combined filtrates are concentrated in the reactor until the temperature in the reactor is 70° C. (distillation temperature 66° C.) at 800 mbar. The remanence (12.8 kg) is further concentrated on a rotavapor to approximately 10 l. Finally, the mixture is fractionally distilled at atmospheric pressure, and the product is collected at 163-4° C. Yield 5.3 kg (72%). NMR complies with the structure.

Example 5

Synthesis of trans-1-((1R,3S)-6-chloro-3-phenylindan-1-yl)-3,3-dimethylpiperazinium (Compound I) Hydrogen Maleate Salt Cis-(1S,3S)-3,5-dichloro-1-phenylindan (VI, LG=Cl) (240 g) is dissolved in butan-2-one (1800 ml). Potassium carbonate (272 g) and 2,2-dimethyl piperazine (prepared in Example 4) (113 g) are added and the mixture is heated at reflux temperature for 40 h. To the reaction mixture is added diethyl ether (2 l) and hydrochloric acid (1M, 6 l). The phases are separated, and pH in the water phase is lowered from 8 to 1 with concentrated hydrochloric acid. The water phase is used to wash the organic phase once again in order to ensure, that all product is in the water phase. Sodium hydroxide (28%) is added to the water phase until pH is 10, and the water phase is extracted twice with diethyl ether (2 l). The diethyl ether extracts are combined, dried with sodium sulphate, and evaporated to dryness using a rotary evaporator. Yield 251 grams of the title compound as an oil. Cis/trans ratio, 18:82 according to NMR. The crude oil (ca. 20 grams) is further purified by flash chromatography on silicagel (eluent: ethyl acetate/ethanol/triethylamine 90:5:5) followed by evaporation to dryness on a rotary evaporator. Yield 12 grams of the title compound as an oil (cis/trans ratio, 10:90 according to NMR). The oil is dissolved in ethanol (100 ml), and to this solution is added a solution of maleic acid in ethanol to pH 3. The resulting mixture is stirred at room temperature for 16 hours, and the formed precipitate is collected by filtration. The volume of ethanol is reduced and another batch of precipitate is collected. Yield 3.5 gram solid (no cis isomer is detected according to NMR) of the title compound. Enantiomeric excess according to CE is >99%. Melting point 175-178° C. NMR complies with the structure.

Example 6

Screening Conditions for the Resolution of 6-chloro-3-phenylindan-1-one (IV) by Super Critical Fluid Chromatography A series of columns is screened for the ability of resolving (IV) using a Gilson SF3 Supercritical Fluid Chromatography System. Eluent: Different solvents containing 0.1% diethylamine are used as modifier (30%), the flow is 4 ml/min, the pressure is 200 bar, and the column is kept at room temperature. Detection is performed using a Gilson UV/VIS-831 detector at 254 nm. The retention time of the two enantiomers ($RT_1$ and $RT_2$) and the width in half height of the two peaks ($\omega_1$ and $\omega_2$) are calculated using Gilson Unipoint, version 3.2, software. The table below gives the resolution ($R_s$) calculated for the individual columns with a series of modifiers; $R_s$ is calculated from the formula $R_S = 2(RT_2 - RT_1)/(\omega_1 + \omega_2)$

| Column | | $R_S$ | | | |
|---|---|---|---|---|---|
| Name | Dimensions[a] | Methanol | Ethanol | Isopropanol | Acetonitril |
| Chiralpak ® AD-H | 4.6, 250, 5 | 17.1 | 10.0 | 2.0 | 19.1 |
| Chiralpak ® AS-H | 4.6, 250, 5 | 3.5 | 4.0 | 4.9 | 3.6 |
| Chiralcel ® OD-H | 4.6, 250, 5 | 4.0 | 3.2 | 2.8 | — |
| Chiralcel ® OJ-H | 4.6, 250, 5 | 0.7 | 0.0 | 0.0 | — |
| Chiralpak ® IA | 4.6, 250, 5 | 5.4 | 2.8 | 0.6 | 2.6 |
| (R,R)-Whelk-O 1 ® | 4.6, 250, 5 | 1.0 | 1.1 | 1.7 | — |

[a]Internal Diameter (mm), Column length (mm), particle size (μm)

Example 7

Resolution of 6-chloro-3-phenylindan-1-one (IV) by Super Critical Fluid Chromatography The resolution is performed using the Berger Multigram II Prep-SFC system with a CHIRALPAK® AD-H column, 20 mm ID×250 mm L, 5 μm. Eluent: Ethanol is used as modifier (20%), the flow is 50 ml/min, the pressure is 100 bar, and the column is kept at 35° C. Detection is performed using a UV detector at 230 nm. A Berger separator is used for lo fraction collection and decompression. The equipment is controlled by SFC Pronto software. The two enantiomers have the retention time 3.9 min. (IVa) and 4.8 min. (IVb). The racemic ketone (IV) is injected as a solution in acetonitril (55 g of (IV) in 800 ml acetonitril); 500 μl of this solution is injected with intervals of 132 seconds. All the fractions containing compound (IVa) are combined and decompressed giving a solution of (IVa) in ethanol, and all the fractions containing compound (IVb) are combined and decompressed as well.

Compound (IVa) is isolated by evaporating the solution on a rotary evaporator, and drying the residue in a vacuum oven at 40° C. Yield 25.6 g (47%) of solid. Melting point 110.8° C., NMR conforms to structure, $[\alpha]_D^{20}$ +72.65° (c=1.0, methanol). CHN calculated for $C_{15}H_{11}OCl$: C, 74.23; H, 4.57; found: C, 74.09; H, 4.70.>99% ee according to the chiral analysis.

Compound (IVb) is isolated in the same way, giving 23.9 g (43%) of solid. Melting point 110.6° C., NMR conforms to structure, $[\alpha]_D^{20}$ −70.33 (c=1.0, methanol). CHN calculated for $C_{15}H_{11}OCl$: C, 74.23; H, 4.57; found: C, 73.79; H 4.70.>99% ee according to the chiral analysis.

Example 8

Synthesis of (1S,3S)-6-chloro-3-phenylindan-1-ol (Va) by Reduction of Enantiomeric Pure (IVa)

(S)-6-chloro-3-phenylindan-1-one (IVa) (isolated as in example 7) (23 g) is added in small portions to a suspension of sodium borohydride (1.6 g) in ethanol (160 ml) at 3-5° C. After the addition has been finalised, the mixture is allowed to reach room temperature. The reaction mixture is stirred for 2.75 hours, where after it is evaporated to dryness. The residue is dissolved in a mixture of water (150 ml) and ethyl acetate (200 ml), the phases are separated, and the water phase is extracted with ethyl acetate (100 ml). The organic phases are combined, washed with water (100 ml), dried with magnesium sulphate, filtered and evaporated to dryness. The residue is recrystallised from heptanes (250 ml), giving 20.9 g (90%) of the title product as a solid. Melting point 108.9° C., NMR conforms to structure, $[\alpha]D^{20}$ +48.30° (c=1.0, methanol). CHN calculated for $C_{15}H_{13}OCl$: C, 73.62; H, 5.35; found: C, 73.55; H, 5.29. >99% ee according to the chiral analysis.

Example 9

Synthesis of (1S,3S)-3,5-dichloro-1-phenylindan (VI, LG=Cl)

A solution of (1S,3S)-6-chloro-3-phenylindan-1-ol (Va) (17 g) (synthesized as in example 8) in tetrahydrofuran (130 ml) is cooled with an ice bath. Thionyl chloride (9.9 g) in tetrahydrofuran (50 ml) is added drop wise at 4-5° C., and then the mixture is stirred over night at ambient temperature. A mixture of water and ice (approximately 25 ml) is added, and stirring is continued until all the ice has melted. The phases are separated, and the organic phase is washed twice with sodium bicarbonate (5% in water, 25 ml). The water phases are then combined, extracted with the organic phase, and then extracted with ethyl acetate (50 ml). The organic phases are then combined, dried with magnesium sulfate, filtered, and evaporated to dryness using a rotary evaporator. Yield 18.7 g (102%) of the title compound as an oil, which partly solidifies. The content of (1S,3R)-3,5-dichloro-1-phenylindan is 18% according to NMR.

Example 10

Synthesis of trans-1-((1R,3S)-6-chloro-3-phenylindan-1-yl)-3,3-dimethylpiperazine (Compound I)

A mixture of (1S,3S)-3,5-dichloro-1-phenylindan (VI, LG=Cl) (18 g) (synthesised as in example 9), potassium carbonate (20.8 g), 2,2-dimethylpiperazine, and methyl ethyl ketone (135 ml) is heated to reflux over night. After cooling to room temperature, diethyl ether (150 ml) and hydrochloric acid (1 M, 450 ml) are added, and the mixture is stirred for a few minutes. The phases are separated, and the pH in the water phase is adjusted from 1 to 12 using sodium hydroxide (28%). The water phase is extracted with diethyl ether (two times 170 ml). All the organic phases are combined, dried with magnesium sulphate, filtered, and evaporated using a rotary evaporator. Yield 20.7 g (89%) of the title compound as an oil. The content of the cis isomer is 19% according to NMR.

Example 11

Synthesis of trans-4-((1R,3S)-6-chloro-3-phenylindan-1-yl)-1,2,2-trimethylpiperazinium (IX) Hydrogen Fumarate Trans-1-((1R,3S)-6-chloro-3-phenylindan-1-yl)-3,3-dimethylpiperazine (I, synthesised as in example 10) is stirred with formic acid (15.2 ml) and formaldehyde (37% in water, 12.5 ml), and heated on an oil batch (temperature 110° C.) for 1½ hour. Water is added to the reaction mixture after cooling to room temperature, and pH is adjusted to approximately 14 with sodium hydroxide (28%). The product is extracted with diethyl ether and then ethyl acetate, adding sodium hydroxide (28%) in between the extractions, if the pH becomes lower than 12. The organic phases are combined, dried with sodium sulphate, filtered, and evaporated to dryness, using a rotary evaporator. Yield 10.9 g (100%) of (IX) as an oil, containing 20% of the cis form according to NMR.

The oil (10 g) is heated with 1-propanol (150 ml), giving a solution. Fumaric acid (3.3 g) is added, and heating is continued until all is dissolved. The mixture is cooled to room temperature and seeded, whereby the product precipitates. The solid is isolated by filtration, washed with a small amount of 1-propanol, and dried in a vacuum oven at 40° C. Yield 6.85 g (52%). Melting point 193.3° C., NMR conforms to structure, $[\alpha]_D^{20}$ −15.2° (c=1.0, methanol). Contains 4% of the cis form according to CE, the other two diastereoisomers are not detected (i.e. the content is below 1%). CHN calculated for $C_{26}H_{31}N_2O_4Cl$: C, 66.30; H, 6.63; N, 5.95; found: C, 65.96; H, 6.61; N, 5.57. >98% ee according to CE.

Example 12

Synthesis of Enantiomeric Pure (R)-6-chloro-3-phenylindan-1-one (IVb) by Oxidation of (1R,3R)-6-chloro-3-phenylindan-1-ol (Vb)

Pyridinium chlorochromat (66.1 g) is added to a solution of (1R,3R)-6-chloro-3-phenyl-indan-1-ol (Vb) (isolated as in example 1a) (50.0 g) in dichloromethane (840 ml), and the mixture is stirred at ambient temperature for two hours. The mixture is filtered, and the residue in the vessel is washed twice with dichloromethane (200 ml), which is is used to wash the filter cake as well. The combined filtrates are evaporated to dryness, using a rotary evaporator. The residue is stirred with sodium hydroxide (2 M, 1 l) and ethyl acetate (750 ml) for ½ an hour. The phases are separated, and the water phase is extracted with ethyl acetate (500 ml). The combined organic phases are washed twice with sodium hydroxide (2 M, 250 ml), and 25% sodium chloride (250 ml). Then the organic phase is stirred with magnesium sulphate (60 g), charcoal (1.4 g), and silica gel 60 (0.06-0.2 mm, 5 g), filtered, and evaporated to dryness using a rotary evaporator. The residue (31.5 g) is recrystallised from 2-propanol (125 ml); the product is isolated by filtration and washed with 2-propanol (40 ml). Drying in a vacuum oven at 50° C. gives 26.0 g (53%) of the product as a solid. Melting point 110.8° C., NMR conforms to structure, $[\alpha]_D^{20}$ −75.6° (c=1.0, methanol). CHN calculated for $C_{15}H_{11}OCl$: C, 74.23; H, 4.57; N 0.00; found: C, 73.89; H, 4.71; N, 0.05. 99.2% ee according to the chiral analysis.

The reaction was repeated twice giving 48 g of the product with 99.6% ee, and 48 g of the product with 98.9% ee, respectively.

Example 13

Screening of Bases for the Racemisation of (R)-6-chloro-3-phenyl-indan-1-one (IVb)

The bases used are from Aldrich: Butyl lithium (BuLi) catalogue no. 18,617-1, tert-butyl lithium (tBuLi) catalogue no. 18,619-8, potassium tert-butoxide (KOtBu) catalogue no. 32,865-0, Lithium tert-butoxide (LiOtBu) catalogue no. 398195, sodium tert-butoxide (NaOtBu) catalogue no. 35,927-0, lithium bis(trimethylsilyl)amide (LiHMDS) catalogue no. 225770, sodium bis(trimethylsilyl)amide (NaHMDS) catalogue no. 24,558-5, and potassium bis(trimethylsilyl)amide (KHMDS) catalogue no. 324671. Lithium diisopropylamide is made from diisopropylamine (Sigma-Aldrich catalogue no. 386464) and BuLi just before use in every experiment.

The following procedure is typical for the experiments and illustrates the use of LDA and the use of two different bases:

A mixture of diisopropylamine (437 µl) and tetrahydrofuran (THF) (4 ml) is stirred under nitrogen and cooled with a batch of dry ice and acetone. Butyl lithium (BuLi) (1.6 M in hexanes, 1.60 ml) is added over 5 minutes. Stirring is continued for 10 minutes, and then the cooling batch is replaced with an ice-water batch. After stirring for another 10 minutes, a solution of (R)-6-chloro-3-phenylindan-1-one (IVb) (synthesised as in example 12) (0.50 g) in THF (4 ml) is added drop wise over 5 minutes to the solution of LDA ("the former base", base 1), and stirring at the water-ice batch is continued for ½ an hour. Then BuLi (1.6 M in hexanes) (1.61 ml) ("the latter base", base 2) is added drop wise over 5 minutes, where after stirring at the ice-water batch is continued for 2½ hours, and then hydrochloric acid (4 M, 4 ml) is added. After stirring for 10 minutes, the phases are separated, and the water phase is extracted with ethyl acetate (two times 10 ml). The combined organic phases are washed with sodium chloride (25%, 10 ml), dried with magnesium sulphate, filtered, and evaporated to dryness using a rotary evaporator. Yield 0.47 g (94%) of an oil, the chemical purity is 83% according to LC-MS, and the enantiomeric excess is 1% according to the chiral analysis.

The table below summarises the results obtained:

| Entry | Equivalents of base 1 | Base 1 | Equivalents of base 2 | Base 2 | Time[1] hr | Purity of raw product % | ee[2] % |
|---|---|---|---|---|---|---|---|
| 1 | 2.25 | LDA[3] | N/A | N/A | 2.5 | 91 | 2 |
| 2 | 2.25 | KOtBu | N/A | N/A | 2.5 | 38 | −10 |
| 3 | 2.25 | BuLi | N/A | N/A | 2.5 | 39 | 5 |
| 4 | 2.25 | tBuLi | N/A | N/A | 2.5 | 40 | −13 |
| 5 | 1.25 | LDA[4] | 1.25 | BuLi | 2.5 | 83 | 1 |
| 6 | 1.25 | LDA[4] | 1 | KOtBu | 2.5 | 88 | 0 |
| 7 | 1.25 | LDA[4] | 1.25 | tBuLi | 2.5 | 88 | −4 |
| 8 | 1.25 | LiHMDS | 1 | KOtBu | 2.5 | 86 | 1 |
| 9 | 1.25 | LiOtBu | 1 | KOtBu | 2.5 | 93 | 0 |
| 10 | 1.25 | LDA[5] | 1 | BuLi | 0.5 | 82 | 2 |
| 11 | 1.25 | LDA[5] | 1 | BuLi | 1 | 93 | 2 |
| 12 | 1.25 | LDA[5] | 1 | BuLi | 2.5 | 90 | −3 |
| 13[6] | 1.25 | LDA[5] | 1 | BuLi | 0.5 | 85 | 2 |
| 14[6] | 1.25 | LDA[5] | 1 | BuLi | 1 | 85 | 2 |
| 15[6] | 1.25 | LDA[5] | 1 | BuLi | 2.5 | 86 | −1 |

[1] Indicating the time for stirring at 0° C. after all has been mixed.
[2] Enantiomeric excess; a negative sign indicates, that IVa is in excess, impurities in the sample may interfere with the analysis.
[3] LDA is made using 2.50 equivalents of diisopropylamine and 2.25 equivalents of BuLi.
[4] LDA is made using 1.50 equivalents of diisopropylamine and 1.25 equivalents of BuLi.
[5] LDA is made using 1.25 equivalents of diisopropylamine and 1.50 equivalents of BuLi.
[6] In these experiments, all BuLi - also the amount indicated as base 2 - is added from the beginning of the experiments, before the addition of compound IVb.

Example 14

Scale up of Racemisation of (R)-6-chloro-3-phenyl-indan-1-one (IVb)

The bases used are the same as in example 13.
A representative procedure is as follows:
Diisopropylamine (6.25 g) is dissolved in tetrahydrofuran (THF) (160 ml), and the mixture is cooled with an dry ice/acetone batch while stirring under nitrogen. Butyl lithium (1.6 M in hexanes, 33 ml) is added slowly keeping the temperature below −60° C. Stirring is continued for 5 minutes at the dry ice/acetone batch, which is then replaced by an ice/water batch. The mixture is stirred for 10 minutes at −10 to 0° C., where after a solution of (R)-6-chloro-3-phenylindan-1-one (IVb) (synthesised as in example 12) (10.0 g) in THF (80 ml) is added slowly keeping the temperature below 5° C. After stirring for approximately ½ an hour, butyl lithium (1.6 M in hexanes, 33 ml) is added slowly, keeping the temperature below 5° C. After stirring at 0-5° C. for 2½ hours, hydrochloric acid (4 M, 100 ml) is added slowly. The phases are separated, and the water phase is extracted two times with ethyl acetate (100 ml). The combined organic phases are washed with 25% sodium chloride (100 ml), and stirred for 10 minutes with magnesium sulphate (26 g), charcoal (1 g), and silica gel (2.6 g). After filtration, the organic phase is evaporated to dryness using a rotary evaporator. The residue is recrystallised from 2-propanol (40 ml). The product is isolated by filtration, washed with ice cold 2-propanol (20 ml), and dried in the vacuum oven at 50° C. over night. Yield 5.85 g (60%). Melting point 95.2° C., NMR conforms to structure, $[\alpha]_D^{20}$ −1.1° (c=1.0, methanol). CHN calculated for $C_{15}H_{11}OCl$: C, 74.23; H, 4.57; found: C, 74.29; H, 4.62.-1.0% ee according to the chiral analysis. Purity 97% according to LC-MS.

The results are summarised in the table below:

| Entry | Equivalents of base 1 | Base 1 | Equivalents of base 2 | Base 2 | Time[1] hr | Yield % | Purity % | ee[2] % |
|---|---|---|---|---|---|---|---|---|
| 1 | 2.25 | LDA[3] | N/A | N/A | 2.5 | 53 | 97 | −3 |
| 2 | 1.25 | LDA[4] | 1.25 | BuLi | 2.5 | 60 | 97 | −1 |
| 3 | 1.25 | LDA[4] | 1 | KOtBu | 2.5 | 76 | 87 | 0 |
| 4 | 1.25 | LiOtBu | 1 | KOtBu | 2.5 | 70 | 79 | −2 |
| 5 | 1.25 | LDA[5] | 1 | BuLi | 2.5 | 70 | 97 | 0 |
| 6[6] | 1.25 | LDA[6] | 1.25 | BuLi | ½ | 59 | 96 | 0 |

[1] Indicating the time for stirring at 0° C. after all has been mixed.
[2] Enantiomeric excess; a negative sign indicates, that IVa is in excess.
[3] LDA is made using 2.50 equivalents of diisopropylamine and 2.25 equivalents of BuLi.
[4] LDA is made using 1.50 equivalents of diisopropylamine and 1.25 equivalents of BuLi.
[5] LDA is made using 1.25 equivalents of diisopropylamine and 1.50 equivalents of BuLi.
[6] In this experiment, all BuLi - also the amount indicated as base 2 - is added from the beginning of the experiment, before the addition of compound IVb; i.e. 1.25 equivalents of diisopropylamine and a total of 2.50 equivalents of BuLi is used.

The invention claimed is:

1. A method for manufacturing a compound of formula I (Compound I) or a salt thereof, the method comprising:
   resolving the racemic compound of formula (IV) (Compound IV) using chiral chromatography; and
   converting the enantiomer of formula IVa (Compound IVa) obtained thereby to the compound of formula I, wherein formula I, formula IV and formula IVa are as follows:

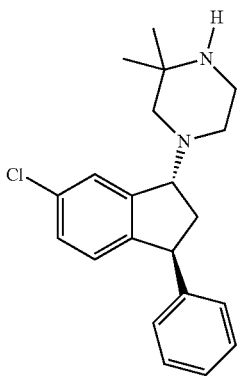
(I)

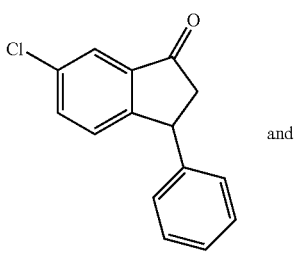
(IV) and

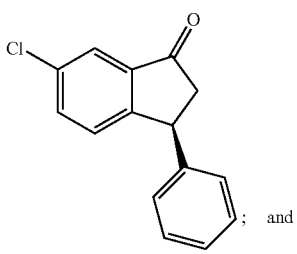
(IVa) ; and the conversion includes the use of a 2,2-dimethylpiperazine analog.

2. The method of claim 1, wherein the conversion includes the compound of formula IVa being converted into the corresponding alcohol Va having cis configuration, wherein formula Va is as follows:

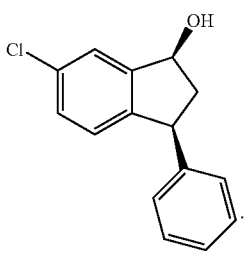
(Va)

3. The method of claim 2, wherein the conversion includes converting the alcohol group of the cis-alcohol of formula Va to a leaving group LG, resulting in a compound of formula VI (Compound VI):

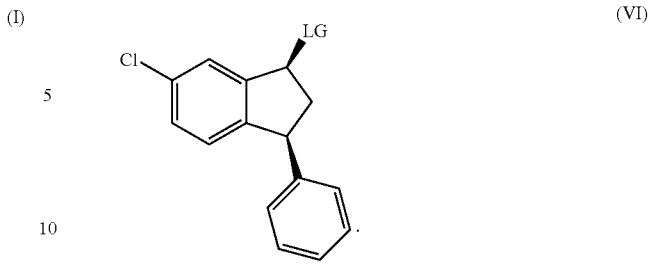
(VI)

4. The method of claim 3, wherein LG is a halogen or a sulfonate.

5. The method of claim 3, wherein Compound VI is precipitated from a suitable solvent 6. The method of claim 5, wherein LG is a halogen and the solvent is an alkane.

7. The method of claim 3, wherein Compound VI is reacted with 2,2-dimethylpiperazine to obtain Compound I.

8. The method of claim 7, wherein Compound I is precipitated as a salt.

9. The method of claim 8, wherein the salt is a fumarate salt, a maleate salt or a hydrochloride salt of Compound I.

10. The method of claim 7, wherein Compound 1 is isolated as a free base.

11. The method of claim 3, comprising:
reacting Compound VI with 1-protected 2,2-dimethylpiperazine of formula VII (Compound VII), wherein PG is a protection group, thereby obtaining a compound of formula VIII (Compound VIII); and
deprotecting Compound VIII to obtain Compound I,
wherein Compound VII and Compound VIII are as follows:

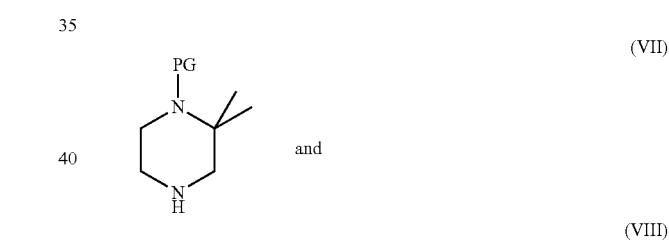
(VII) and

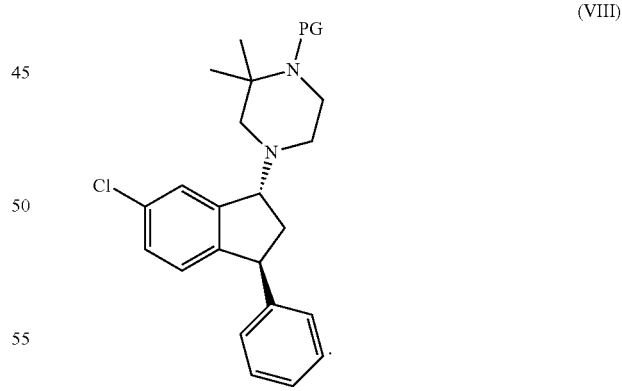
(VIII)

12. The method of claim 1, wherein compound IVa is obtained by resolution of a racemic compound IV using chiral chromatography.

13. The method of claim 12, wherein the chiral chromatography is performed using chiral liquid chromatography.

14. The method of claim 12, wherein the chiral chromatography is performed on a chiral stationary phase.

15. The method of claim 14, wherein the chiral stationary phase is silica gel coated with modified amylose.

16. The method of claim 15, wherein the modified amylase is amylose tris-[(S)-α-methylbenzylcarbamate].

17. The method of claim 16 further comprising a solvent that comprises: a mixture of n-heptane and ethanol; and optionally N,N-diethylamine.

18. The method of claim 12, wherein the chiral chromatography is performed using subcritical fluid chromatography or supercritical fluid chromatography.

19. The method of claim 18, wherein the subcritical fluid chromatography or supercritical fluid chromatography is performed on a chiral stationary phase.

20. The method of claim 19, wherein the chiral stationary phase is silica gel coated with a chiral polymer, silica gel with an immobilized chiral polymer, or silica gel with a covalently bound chiral monomer.

21. The method of claim 20, wherein the chiral polymer of the coated silica gel is amylose tris (3,5-dimethylphenylcarbamate), amylose tris [(S)-α-methylbenzylcarbamate], cellulose tris (3,5-dimethylphenylcarbamate) or cellulose tris (4-methylbenzoate), the immobilized chiral polymer is amylose tris (3,5- dimethylphenylcarbamate), and the covalently bound chiral monomer is 3,5-dinitrobenzoyl tetrahydrophenanthrene amine.

22. The method of claim 20, wherein the chiral polymer of the coated silica gel is amylose tris (3,5-dimethylphenylcarbamate).

23. The method of claim 19, further comprising an eluent having a modifier selected from the group consisting of methanol, ethanol, isopropanol, and acetonitrile; and optionally having diethylamine.

24. The method of claim 1, further comprising recycling Compound IVb by converting enantiomerically enriched compound IVb into essentially racemic compound IV, wherein IVb and IV are:

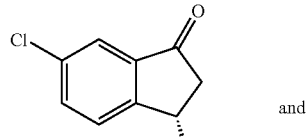

and

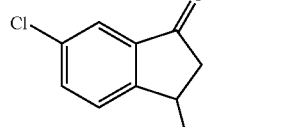

.

25. The method of claim 24, wherein the conversion is obtained by using a base or a mixture of two or more bases.

26. The method of claim 24, wherein the conversion is obtained by using one or more equivalent of a non-nucleophilic base, followed by adding a catalytic amount, or one or more equivalent, of the same or another base.

27. A method for the conversion of an enantiomerically enriched compound IVb into essentially racemic compound IV, wherein IVb and IV are:

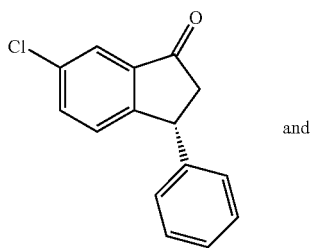

and

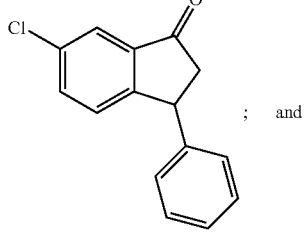

; and the conversion is obtained by using one or more equivalent of a non-nucleophilic base, followed by adding a catalytic amount, or one or more equivalent, of the same or another base.

28. The method of claim 26, wherein the conversion is obtained by using one or more equivalent of a non-nucleophilic base selected from the group consisting of an amide, a metal bis-silylamide, and an metal alkoxide, followed by adding a catalytic amount, or one or more equivalent, of the same or another base selected from the group consisting of an amide, a metal bis-silylamide, an metal alkoxide, an alkyl metal, and a mixture thereof.

29. The method of claim 28, wherein the non-nucleophilic base is selected from the group consisting of lithium diisopropylamide (LDA), lithium bis(trimethylsilyl)amide (LiHMDS), and lithium tert-butoxide.

30. The method of claim 28, wherein the non-nucleophilic base is selected from the group consisting of lithium diisopropylamide (LDA), potassium tert-butoxide, butyl lithium, and tert-butyl lithium.

31. The method of claim 24, wherein non-nucleophilic base and the same or another base are present from the start of the method.

32. The method of claim 24, wherein the essentially racemic compound IV is recrystallized from a suitable solvent.

33. The method of claim 1, wherein Compound I is replaced by Compound IX of formula (IX):

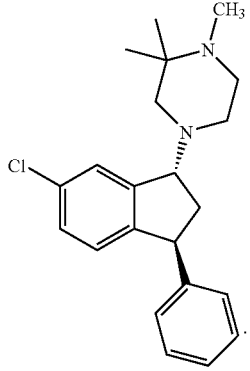

.

34. The method according to claim 33, wherein Compound DC is precipitated as a succinate salt or a malonate salt of Compound IX.

35. The method according to claim 34, wherein the salt is crystalline.

36. The method of claim 35, wherein the salt is formulated into a pharmaceutical composition.

37. The method of claim 4, wherein the halogen is Cl or Br.

38. The method of claim 37, wherein the halogen is Cl.

39. The method of claim 4, wherein the sulfonate is a tosylate or a mesylate.

40. The method of claim 6, wherein the halogen is Cl and the solvent is heptane.

41. The method of claim 18, wherein the chiral chromatography is performed using supercritical fluid chromatography.

42. The method of claim 23, wherein diethylamine is present in an amount of about 0.1%.

43. The method of claim 28, wherein the amide is a dialkylamide.

44. The method of claim 43, wherein the dialkylamide is selected from the group consisting of a lithium diethylamide, a lithium diisopropylamide, a lithium tetramethylpiperidide, and a suitable lithium diisopropylamide (LDA).

45. The method of claim 28, wherein the metal bis-silylamide is an alkali bis(trimethylsily)amide.

46. The method of claim 45, wherein the alkali bis(trimethylsilyl)amide is lithium bis-silylamide or a suitable lithium bis(trimethylsilyl)amide.

47. The method of claim 28, wherein the metal alkoxide is a metal methoxide, a metal ethoxide, a metal tert-butoxide, or a suitable alkali alkoxide.

48. The method of claim 47, wherein the suitable alkali alkoxide is a lithium alkoxide or a potassium alkoxide.

49. The method of claim 48, wherein the lithium alkoxide is lithium tert-butoxide.

50. The method of claim 48, wherein the potassium alkoxide is potassium tert-butoxide.

51. The method of claim 28, wherein the alkyl metal is a suitable alkyl lithium.

52. The method of claim 51, wherein the suitable alkyl lithium is butyl lithium or tert-butyl lithium.

53. The method of claim 32, wherein the suitable solvent is an alcohol.

54. The method of claim 53, wherein the alcohol is a $C_{1-6}$-alcohol.

55. The method of claim 54, wherein the $C_{1-6}$-alcohol is ethanol, 2-propanol or a mixture thereof.

* * * * *

UNITED STATES PATENT AND TRADEMARK OFFICE
CERTIFICATE OF CORRECTION

PATENT NO. : 8,569,499 B2  
APPLICATION NO. : 11/816383  
DATED : October 29, 2013  
INVENTOR(S) : Allan Carsten Dahl et al.

Page 1 of 1

It is certified that error appears in the above-identified patent and that said Letters Patent is hereby corrected as shown below:

In the Claims:

Claim 24, at column 27, line 34, to recite "IVb" in lieu of "Wb".

Claim 34, at column 29, line 2, to recite "IX" in lieu of "DC".

Signed and Sealed this
Twentieth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,569,499 B2 | Page 1 of 1 |
| APPLICATION NO. | : 11/816383 | |
| DATED | : October 29, 2013 | |
| INVENTOR(S) | : Dahl et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this
Thirty-first Day of March, 2015

Michelle K. Lee
*Director of the United States Patent and Trademark Office*